(12) United States Patent
Weber et al.

(10) Patent No.: US 8,815,570 B2
(45) Date of Patent: Aug. 26, 2014

(54) MICROALGAE EXTRACT CONTAINING OMEGA 3-POLYUNSATURATED FATTY ACIDS AND METHOD FOR EXTRACTING OIL FROM MICRO-ORGANISMS

(75) Inventors: Andreas Weber, Grefrath (DE); Nieves Gonzalez Ramon, Delft (NL)

(73) Assignee: Feyecon B.V., Haarlem (NL)

( * ) Notice: Subject to any disclaimer, the term of this patent is extended or adjusted under 35 U.S.C. 154(b) by 586 days.

(21) Appl. No.: 13/122,491

(22) PCT Filed: Oct. 2, 2009

(86) PCT No.: PCT/NL2009/000192
§ 371 (c)(1),
(2), (4) Date: Jun. 27, 2011

(87) PCT Pub. No.: WO2010/039030
PCT Pub. Date: Apr. 8, 2010

(65) Prior Publication Data
US 2011/0251278 A1   Oct. 13, 2011

(30) Foreign Application Priority Data
Oct. 2, 2008   (EP) .................................. 08165766

(51) Int. Cl.
*C11C 1/00*   (2006.01)
*A23D 7/00*   (2006.01)
*A61K 31/00*   (2006.01)

(52) U.S. Cl.
USPC ........................ 435/271; 426/602; 514/560

(58) Field of Classification Search
USPC .......................... 426/602; 435/271; 514/560
See application file for complete search history.

(56) References Cited

U.S. PATENT DOCUMENTS

2008/0175975 A1   7/2008  Fabritius

FOREIGN PATENT DOCUMENTS

| EP | 1 178 118 A | 2/2002 | | |
|---|---|---|---|---|
| EP | 1178118 A1 | * | 2/2002 | ............... C12P 7/64 |
| WO | WO 9743362 A | 11/1997 | | |
| WO | WO 9743362 A1 | * | 11/1997 | ............... C11B 3/00 |

OTHER PUBLICATIONS

Ramirez Fajardo Antonio et al: "Lipid extraction Irom the microalgaPhaeodactylum tricornutum" European Journal of Lipid Science and Technology, vol. 109, No. 2, 2007, pp. 120-126.*
Fajardo, et al., "Lipid extraction from the microalga Phaeodactylum tricornutum", European Journal of Lipid Science and Technology, 109:120-126 (2007).
Medina, et al., "Downstream Processing of Algal Polyunsaturated Fatty Acids", Biotechnology Advances, 16:517-580 (1998).
Belarbi, et al., "A Process for High Yield and Scaleable Recovery of High Purity Eicosapentaenoic Acid Esters From Microalgae and Fish Oil", Enzyme and Microbial Technology, 26:516-529 (2000).

* cited by examiner

*Primary Examiner* — Deborah D Carr
(74) *Attorney, Agent, or Firm* — Browdy and Neimark, PLLC

(57) ABSTRACT

The present invention relates to a biphasic microalgae extract comprising 15-95 wt. % of an aqueous phase and 5-85 wt. % of an oil phase, said extract containing at least 1% by weight of total fatty acids of $\omega$3-fatty acids selected from the group consisting of eicosapentaenoic acid (EPA), docosahexaenoic acid (DHA) and combinations thereof, said extract further being characterized in that it contains: • 40-100% by weight of the oil phase of lipids selected from triglycerides, diglycerides, monoglycerides, phosphatides, free fatty acids and combinations thereof; • 0.01-10% of carotenoids by weight of the oil phase; • 0.5-10% of sodium chloride by weight of the aqueous phase; • 0-3 wt. % of non-dissolved material other than dispersed droplets of aqueous phase or oil phase; and • 0-10% of $C_{1-5}$ monoalcohol by weight of the aqueous phase. Together the aqueous phase and oil phase of the biphasic extract contain essentially all the lipid material that was originally contained in the microalgae biomass, i.e. both apolar lipids (e.g. triglycerides, free fatty acids) and polar lipids (e.g. glycolipids, phospholipids). The invention also provides processes for extracting an oil phase from wet biomass of microorganisms. These processes do not require the use of apolar organic solvents and produce a biphasic extract that can easily be downstream processed to produce $\omega$3-PUFA containing oil in high yield.

19 Claims, No Drawings

MICROALGAE EXTRACT CONTAINING OMEGA 3-POLYUNSATURATED FATTY ACIDS AND METHOD FOR EXTRACTING OIL FROM MICRO-ORGANISMS

TECHNICAL FIELD OF THE INVENTION

The present invention relates to a micro-algae extract containing ω3-polyunsaturated fatty acids selected from the group consisting of eicosapentaenoic acid (EPA), docosahexaenoic acid (DHA) and combinations thereof.

The invention also provides processes for extracting an oil phase from wet biomass of micro-organisms, e.g. from wet biomass of micro-algae.

BACKGROUND OF THE INVENTION

Eicosapentaenoic acid (EPA, 20:5n-3) and docosahexaenoic acid (DHA, 22:6n-3) are ω3-polyunsaturated fatty acids that are metabolically active. A large number of scientific studies have produced data suggesting that EPA and/or DHA are beneficial in the prevention and treatment of a variety of medical conditions, including coronary heart disease, blood platelet aggregation, abnormal cholesterol levels etc.

EPA and/or DHA can be sourced from fish oil, e.g. fish oil from cod liver, herring pilchard, menhaden, tuna, saury fish and mullet. However, fish oil fluctuates in price and quality. Furthermore, there are concerns regarding contamination of fish oil with pesticides and heavy metals. Thus, there is increasing interest for another natural source of the aforementioned ω3-fatty acids, i.e. microalgae.

The extraction of ω3-PUFAs from microalgae poses a major challenge. Typically, bioseparation of ω3-PUFAs from microalgae involves removal of insolubles, isolation of products, purification and polishing. The first step in downstream recovery of polyunsaturated fatty acids (PUFAs) from microalgae is extraction. Extraction should be fast, efficient and gentle in order to reduce degradation of the lipids or fatty acids. As explained by Robles Medina et al. (Biotechnology Advances, Vol. 16, No. 3, (1998), 517-580): "The extraction solvents used should be inexpensive, volatile (for ready removal later), free from toxic or reactive impurities (to avoid reaction with the lipids), able to form a two-phase system with water (to remove non-lipids), and be poor extractors of unwanted components (e.g. proteolipids, small molecules).

Several solvent extraction techniques for isolating ω3-PUFAs from microalgae have been described in the prior art. Frequently, microalgae biomass is subjected to cell disruption before being contacted with the extraction solvent in order to maximize recovery of intracellular products. Cell disruption may be achieved by high-pressure homogenization, agitation in the presence of glass and ceramic beads in bead mills, ultrasonication, chemical lysis or by grinding dried biomass. In commercial processes dried lyophilized microalgae biomass is usually used as a starting material for the solvent extraction process as it produces high extraction yields.

It is known in the art that hexane, chloroform, diethyl ether and ethanol can extract ω3-PUFAs such as EPA and DHA. Apolar solvents such as chloroform, hexane or diethyl ether offer the advantage that non-lipid contaminants hardly dissolve in these in solvents. However, these apolar solvents do not completely extract polar lipids (e.g. phosphatides and glycolipids) because of their limited solubility in these solvents. In order to optimize extraction yields, experiments have been conducted with a variety of solvent mixtures, e.g. hexane/ethanol, hexane-isopropanol and chloroform/methanol/water. Ethanol is capable of extracting ω3-PUFAs from microalgae in relatively high yields. However, ethanol will also extract water and a wide range of polar components. This is why it has been advocated to submit ethanol extracts to another solvent extraction with an apolar solvent or an isolation step (e.g. chromatography) to separate a lipid-enriched fraction.

A. R. Fajardo et al. (Eur. J. Lipid Sci. Tehcnol. 109 (2007) 120-126) describes a method for extracting lipids from microalgae (*Phyaeodactylym tricornutum*) comprising the following steps:

combining lyophilized biomass with ethanol and stirring for 24 hours at room temperature;

filtration to produce a crude extract;

addition of water and hexane to the crude extract to produce a biphasic system; and separation of the biphasic system in a hexanic phase and a hydroalcoholic phase.

Existing methods for isolating Ω3-PUFAs from microalgae suffer from a number of drawbacks. First of all, most if not all of these methods employ apolar solvents such as hexane, chloroform or diethyl ether. The handling of these solvents poses a safety hazard as they are highly explosive and/or toxic. Furthermore, these apolar solvents must be essentially completely removed from the final product (ω3-PUFAs containing oil) as only trace levels of these solvents are allowed in food ingredients.

Another drawback of existing isolation methods resides in their complexity, notably the number of isolation steps employed and/or the need for derivatisation of ω3-PUFAs containing lipids.

EP-A 1 178 118 describes a process for obtaining an oil from microbial cells, the process comprising:

a) disrupting the cell walls of the microbial cells to release the oil; and b) separating the oil from at least part of the cell wall debris formed in (a).

The examples of this European patent application describe processes in which a fungus (*Mortierella alpina*) and an alga (*Oypthecodinium cohnii*) are disrupted by high pressure homogenization, followed by centrifugation which produced an oily top layer and a lower aqueous layer containing the cell debris.

SUMMARY OF THE INVENTION

The present inventors have designed alternative processes for isolating ω3-PUFAs from microalgae that avoid at least some of the aforementioned drawbacks. The processes according to the present invention start from wet microalgae biomass, do not require the use of apolar organic solvents and produce a biphasic extract that can easily be downstream processed to produce ω3-PUFA containing oil in high yield or that may be used as such, e.g. in the production of animal feed. The biphasic extract obtained by the present processes comprises an oil phase and an aqueous phase that together contain essentially all the lipid material that was originally contained in the wet biomass, i.e. both apolar lipids (e.g. triglycerides, free fatty acids) and polar lipids (e.g. glycolipids, phospholipids).

Thus, one aspect of the present invention relates to a biphasic microalgae extract comprising an aqueous phase and an oil phase, said extract being characterized in that it contains:

40-100% by weight of the oil phase of lipids selected from triglycerides, diglycerides, monoglycerides, phosphatides, free fatty acids and combinations thereof;

0.01-10% of carotenoids by weight of the oil phase;

0.5-10% of sodium chloride by weight of the aqueous phase;

0-3 wt. % of non-dissolved material other than dispersed droplets of aqueous phase or oil phase; and 0-10% of $C_{1-5}$ monoalcohol by weight of the aqueous phase.

Another aspect of the invention relates to a process of producing a biphasic extract as described above from wet biomass of micro-organisms, followed by extraction of an oil phase, said process comprising:

combining the wet biomass with a solvent containing at least 60 wt. % of $C_{1-5}$ monoalcohol;

isolating a liquid phase from the combination of biomass and solvent, said liquid phase containing 5-85 wt. % of $C_{1-5}$ monoalcohol, 10-85 wt. % of water and at least 5 wt. % of dissolved and/or dispersed components originating from the biomass, including at least 5% of lipids by weight of $C_{1-5}$ monoalcohol;

reducing the concentration of $C_{1-5}$ monoalcohol in the liquid phase to less than 10 wt. % whilst maintaining a water content of at least 15 wt. % to produce an extract containing an aqueous phase and an oil phase; and separating the oil phase from the aqueous phase.

Yet another aspect of the invention relates to an alternative process of extracting an oil phase from a biphasic extract as described herein before, said process comprising:

combining wet microalgae biomass with an enzyme preparation having cellulose, (β-gluconase or β-glucosidase activity;

allowing the enzyme preparation to degrade the cell walls of the microalgae;

isolating from the enzyme treated biomass at least 20% of a liquid by weight of the wet microalgae biomass, said liquid being a biphasic extract comprising 50-90 wt. % of an aqueous phase and 5-50 wt. % of an oil phase; and separating the oil phase from the aqueous phase.

DETAILED DESCRIPTION OF THE INVENTION

Accordingly, a first aspect of the invention relates to a biphasic microalgae extract comprising 15-95 wt. % of an aqueous phase and 5-85 wt. % of an oil phase, said extract containing at least 1% by weight of total fatty acids of ω3-fatty acids selected from the group consisting of eicosapentaenoic acid (EPA), docosahexaenoic acid (DHA) and combinations thereof, said extract further being characterized in that it contains:

40-100% by weight of the oil phase of lipids selected from triglycerides, diglycerides, monoglycerides, phosphatides, free fatty acids and combinations thereof;

0.01-10% of carotenoids by weight of the oil phase;

0.5-10% of sodium chloride by weight of the aqueous phase;

0-3 wt. % of non-dissolved material other than dispersed droplets of aqueous phase or oil phase; and 0-10% of $C_{1-5}$ monoalcohol by weight of the aqueous phase.

The term "biphasic extract" as used herein refers to an extract comprising at least an aqueous phase and an oil phase. Thus, the term "biphasic extract" also encompasses emulsions comprising three or more phases, e.g. a water-in-oil-in-water emulsion or an emulsion containing another phase that is immiscible with the aqueous phase or the oil phase. Preferably, the biphasic extract essentially consist of two separate phases, i.e. the aqueous phase and the oil phase.

Whenever reference is made in here to a fatty acid concentration, unless otherwise indicated, said concentration is calculated by weight of the total amount of fatty acids, including free fatty acids and fatty acids contained in fatty acid esters such as glyceride and phosphate esters.

According to a particularly preferred embodiment, the biphasic microalgae extract comprises 20-90 wt. % of an aqueous phase and 10-80 wt. % of an oil phase. Most preferably, the biphasic microalgae extract comprises 30-85 wt. % of an aqueous phase and 15-70 wt. % of an oil phase.

The oil phase of the present biphasic extract preferably contains 50-100%, more preferably 70-100%, and most preferably 85-100% by weight of the oil phase of lipids selected from triglycerides, diglycerides, monoglycerides, phosphatides, free fatty acids and combinations thereof.

The biphasic extract of the present invention typically contains a considerable amount of carotenoids, e.g. at least 0.03-5%, more preferably at least 0.1% and most preferably at least 0.3% of carotenoids by weight of the oil phase. Typically, the amount of carotenoids contained in the extract will not exceed 5 wt. %. Preferably, the carotenoid content does not exceed 3 wt. %. Likewise, the extract usually contains a considerably amount of sodium chloride. Typically, the biphasic extract contains 0.7-6%, more preferably 0.8-4% of sodium chloride by weight of the aqueous phase;

The benefits of the present invention are particularly pronounced in case a significant fraction of the ω3-fatty acids is contained in the polar lipid fraction, in particular if a significant fraction is contained in phosphatides (e.g. phosphatidyl choline and/or phosphatidyl ethanolamine) and/or glycolipids. According to a preferred embodiment at least 10 wt. %, more preferably at least 20 wt. % and most preferably at least 25 wt. % of the ω3-fatty acids are contained in polar lipids selected from phosphatides, glycolipids and combinations thereof.

Advantageously, the present extract contains 3-50%, more preferably 5-40% of the aforementioned polar lipids by weight of the oil phase. Even more preferably, the present extract contains 3-50%, most preferably 5-40% of phosphatides by weight of the oil phase.

In a preferred embodiment of the present invention the biphasic extract is produced by means of extraction with a solvent having a high content of $C_{1-5}$ monoalcohol, followed by removal of the bulk of said alcohol by means of evaporation. Usually, a small quantity of the $C_{1-5}$ monoalcohol will be retained in the biphasic extract. Typically, the extract contains 0.01-10%, more preferably 0.03-10%, even more preferably 0.1-10%, and most preferably 0.1-5% of $C_{1-5}$ monoalcohol by weight of the aqueous phase. Preferably, the $C_{1-5}$ monoalcohol is selected from the group selected from methanol, ethanol, isopropanol and combinations thereof. Most preferably, the $C_{1-5}$ monoalcohol is ethanol.

As explained herein before, the present invention provides the important advantage that it does not rely on the use of apolar organic solvents. Hence, according to a particularly preferred embodiment, the extract contains less than 0.1 wt. %, even more preferably less than 0.03 wt. % of organic solvents other than $C_{1-5}$ monoalcohol.

The benefits of the present invention may be realized using all kinds of microalgae, provided they contain significant amounts of EPA and/or DHA. According to a preferred embodiment, the microalgae employed in accordance with the present invention are not silicate or calcium secreting species that belong to the diatoms or the genus *Coccolithophores*. Examples of genus/classes of microalgae that can suitably be employed include *Chysophyceae, Xantophyceae, Eustigmatophyceae, Baccilariophyceae, Dinophyceae, Rodophyceae, Phaeophyceae, Chlorophyceae, Prasinophyceae, Cryptophyceae, Botrycoccus, Isochrysis, Tetrasel-* mis, *Neochloris, Scenedesmus, Chlorobotlys, Eustigmatos, Pseudostaurastrum, Vischeria, Monodopsis, Ellipsoidion, Pseudocharaciopsis* and combinations thereof. Even more preferably, the microalgae employed, belongs to a genus or class selected from *Eustigmatophyceae, Chlorophyceae* and combinations thereof. Most preferably, the microalgae employed in accordance with the present invention are selected from *Nannochloropsis gaditana, Isochrysis galbana, Chlorella fusca, Haematococcus pluvialis* and combinations thereof.

The microalgae employed in accordance with the present invention preferably are green microalgae. Accordingly, in a preferred embodiment, the extract contains at least 0.02%, more preferably 0.05% of chlorophyll by weight of the oil phase. Usually, chlorophyll concentration of the extract does not exceed 1% by weight of the oil phase.

The biphasic extract of the present invention may suitably be produced by extracting wet biomass with a $C_{1-5}$ monoalcohol, followed by evaporation of the bulk of said monoalcohol. Such a biphasic extract is characterized in that it can be completely dissolved again in the $C_{1-5}$ monoalcohol that was used the extraction solvent. Thus, in accordance with this embodiment of the invention, advantageously 200 grams of the extract can be fully dissolved in 1 liter of $C_{1-5}$ monoalcohol.

Alternatively, the biphasic extract of the invention can be produced by enzymatically hydrolyzing the cell wall components of wet microalgae biomass, followed by removal of non-soluble material. Such a biphasic extract typically contains at least 1%, preferably at least 3% of hydrolysed cellulosic algae cell wall material by weight of dry matter. Best results are obtained in accordance with this embodiment if a large fraction of the cellulose contained in the original microalgae biomass is hydrolyzed. Advantageously, at least of 50%, more preferably at least 80% of the cellulose contained in the extract is hydrolyzed cellulose.

Preferably, both the aqueous phase and the oil phase of the present biphasic extract contain less than 1 wt. % non-dissolved material other than dispersed droplets of the other phase. Low levels of non-dissolved material are desirable as they facilitate downstream recovery of the ω3-PUFAs EPA and DHA.

Typically, the aqueous phase and the oil phase of the present biphasic extract together represent at least 80 wt. %, preferably at least 90 wt. % and most preferably at least 98 wt. % of the extract.

Another aspect of the invention relates to a process of extracting an oil phase from wet biomass of micro-organisms, the process comprising:
combining the wet biomass with a solvent containing at least 60 wt. % of $C_{1-5}$ monoalcohol, said biomass containing 10-95 wt. % of water and 5-85% by weight of dry matter of lipids selected from triglycerides, diglycerides, monoglycerides, phosphatides, free fatty acids and combinations thereof;
isolating a liquid phase from the combination of biomass and solvent, said liquid phase containing 5-85 wt. % of $C_{1-5}$ monoalcohol, 10-85 wt. % of water and at least 5 wt. % of dissolved and/or dispersed components originating from the biomass, including at least 5% of lipids by weight of $C_{1-5}$ monoalcohol;
reducing the concentration of $C_{1-5}$ monoalcohol in the liquid phase to less than 10 wt. % whilst maintaining a water content of at least 15 wt. % to produce a biphasic extract containing an aqueous phase and an oil phase; and
separating the oil phase from the aqueous phase.

The term "wet biomass" as used herein refers to biomass containing at least 10 wt. % of water. Preferably, the wet biomass contains at least 30 wt. % of water and most preferably more than 50 wt. % of water. The present processes offer the important advantage that they use wet biomass as a starting material which means that drying steps can be avoided. Drying of biomass not only has the disadvantage that it consumes vast quantities of energy, but also has the important drawback that it promotes oxidation of the ω-3 PUFAs contained in the biomass.

According to a particularly preferred embodiment, the cells contained in the wet biomass employed in the present process are not disrupted prior to the combining of said biomass and the $C_{1-5}$ monoalcohol. The inventors have unexpectedly found that it is not necessary to disrupt the microalgae cells (e.g. by high shear homogenisation) in order to achieve high extraction yields. Hence, according to a preferred embodiment, the wet biomass when combined with the $C_{1-5}$ monoalcohol contains at least $10^8$, more preferably at least $10^9$ and most preferably at least $10^{10}$ intact microalgae cells per gram of wet biomass.

The liquid phase that is isolated from the combination of biomass and solvent preferably contains not more than 5 wt. %, more preferably not more than 3 wt. % and most preferably not more than 2 wt. % of non-dissolved material, such as cell debris. The liquid phase may suitably be isolated by means of filtration, decantation and/or centrifugation.

The benefits of the present process are particularly evident in case the wet biomass contains considerable quantities of lipids. According to a particularly preferred embodiment, the wet biomass contains at least 10%, most preferably at least 15% by weight of dry matter of lipids selected from triglycerides, diglycerides, monoglycerides, phosphatides, free fatty acids and combinations thereof.

Besides $C_{1-5}$ monoalcohol the solvent used to extract the wet biomass may contain other solvents such as water and polar organic solvents. Minor amounts of apolar organic solvents may also be contained in the extraction solvent, but as explained herein before, it is preferred not to employ such apolar organic solvents. Even more preferably, the extraction solvent does not contain any organic solvents besides $C_{1-5}$ monoalcohol. According to a particularly preferred embodiment, the extraction solvent contains at least 80 wt. %, most preferably at least 90 wt. % of $C_{1-5}$ monoalcohol.

Examples of $C_{1-5}$ monoalcohols that can suitably be employed in the present process include methanol, ethanol, isopropanol and combinations thereof. Most preferably the $C_{1-5}$ monoalcohol employed is ethanol.

The concentration of the $C_{1-5}$ monoalcohol in the liquid phase can be reduced by a variety of techniques, e.g. evaporation, adsorption, chromatography, solvent extraction etc. In the present process the concentration of $C_{1-5}$ monoalcohol in the liquid phase is advantageously reduced by means of evaporation. Said evaporation may be carried out under reduced pressure and/or elevated temperature.

The above described process is particularly suitable for isolating ω3-PUFAs from wet biomass of micro-organisms. Accordingly, said wet biomass preferably contains at least 1%, more preferably at least 5% by weight of total fatty acids of ω3-fatty acids selected from EPA, DHA and combinations thereof.

Advantageously, the wet biomass employed in the aforementioned process is a biomass of microalgae, preferably a biomass of a microalgae genus or class selected from *Chysophyceae, Xantophyceae, Eustigmatophyceae, Baccilariophyceae, Dinophyceae, Rodophyceae, Phaeophyceae, Chlorophyceae, Prasinophyceae, Cryptophyceae, Botrycoc-* cus, Isocinysis, Tetraselmis, Neochloris, Scenedesmus, Chlorobohys, Eustigmatos, Pseudostaurastrum, Vischeria, Monodopsis, Ellipsoidion, Pseudocharaciopsis and combinations thereof. Even more preferably, the microalgae employed, belongs to a microalgae genus or class selected from Eustigmatophyceae, Chlorophyceae and combinations thereof.

In the above defined process separation of the oil phase from the aqueous phase is suitably achieved by centrifugation and/or decanting. Most preferably, the oil phase is separated by decanting.

Yet another aspect of the invention relates to a process of extracting an oil phase from cell-wall containing microalgae, said oil-phase containing at least 1% by weight of total fatty acids of ω3-fatty acids selected from EPA, DHA and combinations thereof; the process comprising:

combining wet microalgae biomass containing the ω3-fatty acids with an enzyme preparation having cellulase, β-glucanase or β-glucosidase activity;

allowing the enzyme preparation to degrade the cell walls of the microalgae;

isolating from the enzyme treated biomass at least 20% of a liquid by weight of the wet microalgae biomass, said liquid being a biphasic extract comprising 50-95 wt. % of an aqueous phase and 5-50 wt. % of an oil phase; and separating the oil phase from the aqueous phase.

According to a particularly preferred embodiment of the above defined process, the enzyme preparation is combined with the biomass in an amount sufficient to provide at least 1 IU per gram of biomass dry matter of endoglucanase activity and/or at least 0.2 IU per gram of biomass dry matter of units of β-glucanase and/or at least 0.8 IU per gram of biomass dry matter of β-glucosidase activity. Endoglucanase activity is determined using a microplate-based carboxymethylcellulose (CMC) assay as described by Xiao et al (Analytical Biochemistry, 342 (2005), 176-178). One IU of endoglucanase activity is defined as the amount of enzyme that liberates one micromol of reducing sugars (expressed as glucose equivalent) in 1 minute at 50° C. and pH 4.8. One IU of β-glucanase activity is defined as the amount of enzyme that liberates 1 μmol of reducing sugar equivalents (expressed as glucose) per minute at 55° C. and pH 5.0, using β-D-glucan as substrate. Similarly, one IU of β-glucosidase activity is defined as the amount of enzyme that liberates 1 μmol of nitrophenol from para-nitrophenyl-β-D-glucopyranose in 10 minutes at specific assay conditions at 50° C. and pH 4.8.

Enzymatic degradation of the cell walls of the microalgae in accordance with the procedure described above offers the advantage that it is unnecessary to apply mechanical rupture, notably high shear conditions, to lyse the cells. Thus, in a particularly preferred embodiment of this process the wet microalgae biomass is not subjected to mechanical rupture prior to the isolation of the biphasic liquid. Even more preferably, the wet microalgae biomass is not subjected to high shear homogenisation, even more it is not subjected to high shear homogenization at pressures of 100 bar or more. Most preferably, the wet microalgae biomass is not subjected to high shear homogenization at pressures of 80 bar or more.

The wet biomass employed in this process typically has a water content of 10-95 wt. %. More preferably, the wet biomass employed in the processes according to the present invention has a water content of 15-80 wt. %.

In the above defined process a biphasic extract is produced from which an oil phase is isolated by separating it from an aqueous phase. Separation of the oil phase can be achieved in different ways. According to a particularly preferred embodiment, the oil phase is separated from the aqueous phase by centrifugation and/or decanting. Most preferably, the oil phase is separated by decanting. The isolated oil phase obtained by the present process may be subjected to further processing steps in order to remove impurities and to enhance the concentration of EPA and/or DHA. Suitable processing techniques for removing impurities and/or for concentrating EPA and/or DHA are known in the art.

In accordance with a further preferred embodiment, the algae biomass contains at least 75 wt. % biomass of green microalgae, preferably at least 75 wt. % biomass of microalgae belonging to a microalgae genus or microalgae class selected from Chysophyceae, Xantophyceae, Baccilariophyceae, Dinophyceae, Rodophyceae, Phaeophyceae, Chlorophyceae, Prasinophyceae, Ciyptophyceae, Botrycoccus, Isochrysis, Tetraselmis, Neochloris, Scenedesmus, Chlorobohys, Eustigmatos, Pseudostaurastrum, Vischeria, Monodopsis, Ellipsoidion, Pseudocharaciopsis and combinations thereof.

Advantageously, the present processes do not employ any organic solvents other than $C_{1-5}$ monoalcohol. Most preferably said processes employ any organic solvents other than ethanol.

The biphasic extract produced in the aforementioned processes advantageously is a biphasic extract as defined herein before.

Yet another aspect of the invention concerns the use of the biphasic extract of the present invention or the use of an oil phase isolated from said biphasic extract in the production of foodstuffs, beverages, nutritional preparations, pharmaceutical preparations, animal feed or cosmetic products. The biphasic extracts and the isolated oil phase are particularly suited for use in animal feed as the extract or isolated oil phase can be incorporated into the animal feed without the need of any pretreatment. Consequently, in a particularly preferred embodiment, the biphasic extract or the oil phase extracted therefrom is used in the production of animal feed.

Typically, the present use comprises incorporating the biphasic extract or the oil phase in an amount that is equivalent to at least 0.1% by weight of the final product.

The invention is further illustrated by means of the following non-limiting examples.

EXAMPLES

Example 1

Wet microalgae biomass (*Nannochloropsis*) was extracted with ethanol. The *nannochloropsis* strain used was:

*Nannochloropsis gaditana* Lubian (1982); Division: Heterokontophyta, Class: *Eustigmatophyceae*. CCAP 849/5 from the Culture Collection of Algae and Protozoa (CCAP)

Isolator: Lubian (pre 1977); Origin: Marine; Cadiz Bay, Cadiz, Spain Culture: Medium SNA; A; sub

*Nannochloropsis* microalgae were harvested at their exponential growing phase and the cells suspension was centrifuged for the elimination of excess water and salts with a centrifuge of the type Alfa Laval CLARA 80. Hundred grams of the wet biomass so obtained was extracted with 200 g of pure ethanol (99.9%) by stirring the blend of biomass and ethanol for 1 hour at room temperature using an Erlenmeyer flask with a magnetic stirrer and glass stopper. The extract was filtered by suction with the help of a Büchner funnel and the retentate was washed twice with in total 50 g of ethanol. Next, more than 99 wt. % of the ethanol was removed from the filtrate using a rotational evaporator (65° C., 200 mbar). After evaporation, the extract was allowed to cool down to ambient temperature. At this stage phase separation occurred, yielding a biphasic extract comprising:
i. 73 wt. % of an aqueous lower phase containing mainly salts and glucidic components; and
ii. 27 wt. % an oily upper phase with a melting point of approximately 30° C.

The oil phase was separated from the aqueous phase by means of decanting. The total amount of extracted material accounted for 32 wt. % of the original biomass (dry matter). Analysis showed that the lipid upper phase contained 5.5 wt. % eicosapentaenoic acid (EPA).

GC-analysis further showed that palmitic acid, stearic acid and oleic acid were the main fatty acids, together representing 60-70 wt. % of the fatty acids contained in the oil phase.

A sample of the isolated oil phase was subjected to a lipids analysis using a glass column containing 3 g of Silica gel 60 in 5 ml of chloroform. To this end 0.1030 g of the oil phase in 2-3 ml chloroform was applied onto the column, followed by elution with:
- 100 ml chloroform to elute NEUTRAL LIPIDS (sterols, triglycerides, fatty acids);
- 150 ml of acetone: methanol (9:1) to elute GLYCOLIPIDS (cerebrosides, sulfatides, mono- and digalactosyl diglycerides, sterol glycosides) and CERAMIDES and finally
- 100 ml methanol to elute phospholipids.

The composition of the oil phase was found to be as follows:

| | |
|---|---|
| NEUTRAL LIPIDS | 47.05 wt. %. |
| GLYCOLIPIDS AND CERAMIDES | 26.22 wt. %. |
| PHOSPHOLIPIDS | 26.73 wt. % |

Furthermore, it was found that the oil phase contained 2.71 wt. % of cholesterol and 1285 mg/kg of carotene.

Example 2

The retentate obtained from the Buchner funnel after the extraction described in Example 1 was subjected to another extraction with 200 g of pure ethanol (99.9%) at ambient temperature by stirring the extraction mixture for 1 hour in an Erlenmeyer flask with a magnetic stirrer and glass stopper. The extract was filtered by suction with the help of a Buchner funnel and the retentate was washed twice with in total 50 g of ethanol. Next, the ethanol was removed from the filtrate using a rotational evaporator (65° C., 200 mbar) and allowed to cool down to ambient temperature, yielding an oily extract.

The total amount of material extracted during the second extraction accounted for 5.9 wt. % of the original biomass. Analysis further showed that the extract obtained in the second extraction contained 5.1 wt. % EPA. GC-analysis further showed that the fatty acid composition of the second extract was essentially identical to that of the first extract.

The retentate from the second extraction was extracted twice with a mixture of chloroform and methanol to remove any residual lipid material contained therein. The total amount of lipids extracted with this solvent mixture was 4.3% by weight of the extracted mass. The EPA content of the extracted lipids was 1.7 wt. %. The total amount of EPA removed from the wet biomass by the two ethanol extractions and the chloroform/methanol extraction was 13.4% by weight of dry matter. This percentage equals the amount of EPA normally found in Nannochloropsis.

Samples of both the extract obtained from the first extraction described in Example 1 and the extract obtained from the second extraction were subjected to thin layer chromatography. The chromatograms so obtained showed that the first extract mainly consisted of polar lipids, glyco- and phospholipids and that the second extract mostly consists of triglycerides and coloured components (chlorophyles).

Example 3

Examples 1 and 2 were repeated using a different batch of Nannochloropsis wet biomass. The first extraction was found to remove 31.3 wt. % of extracted material from the original biomass (calculated on dry matter), whereas the second extraction removed another 7.3 wt. %

Again, the first extraction yielded a biphasic extract that was separated into an oil phase and an aqueous phase by decanting. The oil phase from the first extraction contained 7.3 wt. % EPA and the extract obtained from the second extraction contained 4.4 wt. % EPA.

Comparative Example A

The same Nannochloropsis strain as was used in Examples 1-3 was homogenized and dried by means of spray drying. Subsequently, 250 g of the dried biomass was subjected to extraction with supercritical carbon dioxide (constant flow rate of 5-5.5 kg/h). During extraction the supercritical carbon dioxide was continously recirculated. Extracted components were removed by expanding the carbon dioxide in an expansion chamber followed by (re)pressurisation of the carbon dioxide to a supercritical state. First, dry biomass was extracted with supercritical carbon dioxide (300 bar, 90° C.). Next, the extraction residue was extracted once more time using supercritical carbon dioxide (150 bar, 50° C. followed by 300 bar, 90° C.)

In Table 1 the extraction conditions and extraction yields are summarised:

TABLE 1

| Extraction conditions | Total amount extracted (on dry mass) | EPA in the extracted oil |
|---|---|---|
| 300 bar, 90° C., 18 h | 23 wt. % | 3.3 wt. % |
| a) 150 bar, 50° C., 5.5 h | 14 wt. % | a) 3.2 wt. % |
| b) 300 bar, 90° C., 5.5 h | | b) 2.8 wt. % |

EPA levels in the extracted oil were significantly lower than those found in the extracted oils of Examples 1-3. It was further found that the residue obtained from the second extraction still contained a substantial amount of EPA (13-16% of the EPA contained in the starting material), despite the long extraction times employed.

Comparative Example B

Two batches of the same Nannochloropsis strain as was used in Examples 1-3 were homogenized and dried by means of spray drying. Subsequently, the dried biomass was extracted at ambient temperature with a mixture of chloroform and methanol using a modified Blight and Dyer method. The wet biomass (20 grams) was mixed with a 1:2 (w/w) chloroform/methanol mixture (75 ml) in an Erlenmeyer flask and shaken vigorously for 3 minutes. Next, 20 ml of chloroform and 20 ml of water were added, followed by 3 hours of stirring. The mixture was transferred to a decanter in which phase separation was allowed to occur during a period of two hours. The lower (chloroformic) phase was recovered and organic solvent was removed using a rotavap. Table 2 summarizes the extraction extraction yields so obtained for each batch of *Nannochloropsis*:

TABLE 2

| Total amount extracted (on dry mass) | EPA in the extracted oil |
|---|---|
| 24.6 wt. % | 6.0 wt. % |
| 20.0 wt. % | 3.2 wt. % |

Extraction with the chloroform/methanol mixture produces high yields of EPA. However, since both chloroform and methanol are toxic, severe safety precautions need to be taken during extraction and complex downstream processing is required to reduce residual solvent levels to levels that are considered food-grade.

Comparitive Example C

Two batches of the same *Nannochloropsis* strain as was used in Examples 1-3 were homogenized and dried by means of spray drying. Subsequently, the dried biomass (15 g) was subjected to extraction with 300 ml of hexane in a Soxhlet extractor at 80° C. for 12 hours. Table 3 summarizes the extraction yields so obtained for each batch of *Nannochloropsis*:

TABLE 3

| Total amount extracted (on dry mass) | EPA in the extracted oil |
|---|---|
| 25.4 wt. % | 3.9 wt. % |
| 23.2 wt. % | 3.9 wt. % |

Hexane extraction produced a very high lipid yield, but the EPA-level in the extracted oils are considerably lower than those found in the extracted oils of Examples 1-3. In addition, it was found that a high proportion of the EPA was retained in the extraction residue (approximately 20%), despite the long extraction times employed.

Example 4

Example 1 was repeated except that this time microalgae biomass of *Chorella fusca* (Division: *Scenedesmus*, origin: fresh water) was extracted with ethanol. The microalgae biomass used (ex Source Ingrepro BV, the Netherlands) was supplied in dry form and was reconstituted with sea water (1:1) prior to extraction. According to specification, the dried biomass has a lipid content of 6-20%, depending on harvesting season.

Following the evaporation on a rotational evaporator and subsequent cooling to ambient temperature, a biphasic extract was obtained that contained 26 wt. % of oil phase and 74 wt. % of aqueous phase. The extraction was found to remove 26.4 wt. % of extracted material from the original biomass (calculated on dry matter).

GC-analysis showed that palmitic acid, stearic acid and oleic acid were the main fatty acids, together representing 60-70 wt. % of the fatty acids contained in the oil phase. A sample of the isolated oil phase was subjected to the same lipids analysis as described in Example 1.

The composition of the oil phase was found to be as follows:

| NEUTRAL LIPIDS | 47 wt. %. |
|---|---|
| GLYCOLIPIDS AND CERAMIDES | 26 wt. %. |
| PHOSPHOLIPIDS | 27 wt. % |

Example 5

Example 4 was repeated, except that this time instead of pure ethanol a 9:1 mixture of ethanol and hexane was used. Following the evaporation on a rotational evaporator and subsequent cooling to ambient temperature, a biphasic extract was obtained that contained 31 wt. % of oil phase and 69 wt. % of aqueous phase. The extraction was found to remove 27.4 wt. % of extracted material from the original biomass (calculated on dry matter).

Example 6

The *Nannochloropsis* strain of Examples 1-3 was subjected to an alternative oil extraction process involving enzymatic treatment of the wet biomass. *Nannochloropsis* microalgae were harvested at their exponential growing phase and the cells suspension was centrifuged for the elimination of excess water and salts with a centrifuge of the type Alfa Laval CLARA 80. Hundred grams of the wet biomass so obtained was introduced in an Erlenmeyer flask and pH was adjusted with acetate buffer to 4.5. Next, an enzyme preparation was added and thoroughly mixed with the biomass. The resulting mixture was maintained at 50° C. with the help of a water bath and stirred gently. The cell suspensions so obtained were filtered over standard Waltman® filter paper to eliminate cell debris and subsequently subjected to mild centrifugation (10 minutes at 2000G). In all cases centrifugation yielded a biphasic extract containing an aqueous phase and an oil phase.

Table 4 specifies the enzyme preparations and conditions that were used as well as the EPA content of the oil phase:

TABLE 4

| Digesting enzyme | Amount of enzyme added | Conditions | EPA in oil phase |
|---|---|---|---|
| Accelerase ® 1000 | 0.05 ml per gram of biomass | 1 hour at 50° C. | 6.2% |
| Accelerase ® 1000 | 0.05 ml per gram of biomass | 5 hours at 50° C. | 6.3% |
| Viscozyme ® L | 1% by weight of dry biomass | 6 hours at 50° C. | 7.3% |
| Celluclast ® BG | 1% by weight of dry biomass | 6 hours at 50° C. | 7.4% |
| Viscozyme ® L + Celluclast ® BG | 1% by weight of dry biomass | 16 hours at 50° C. | 8.9% |

Example 7

Biomass of the following microalgae species was extracted with ethanol:
*Nannochloropsis gaditana* Lubian (1982); Division: *Heterokontophyta*, Class: *Eustigmatophyceae*. CCAP 849/5 from the Culture Collection of Algae and Protozoa (CCAP). Isolator: Lubian (pre 1977). Origin: Marine; Cadiz Bay, Cadiz, Spain. Culture: Medium SNA; A; sub
*Chlorella fusca*. Source Ingrepro BV, The Netherlands, Average lipid content: 6-20% depending on harvesting season. Division: *Scenedesmus*. Origin: fresh water

*Haematococcus pluvialis* Flotow (1844), Division: *Chlorophyta*, Class: *Clorophyceae*, Order: *Volvocales*. CCAP 34/6 from the Culture Collection of Algae and Protozoa (CCAP). Isolator: Droop (1951). Origin: fresh water, rain pool; Ostpicken Island, Tvarmimme, Finland. Culture: Medium EG:JM; A; cryo

*Isochrysis galbana* Parke (1949), Division: *Plymnesiophyta* (*Haptophyta*), Class: *Prymnesiophyciae*. CCAP 927/1 from the Culture Collection of Algae and Protozoa (CCAP). Isolator: Parke (1938); Origin: Marine; fish pond; Port Erin Marine Station, Isle of Man, Britain. Culture: Medium f/2; A; sub The microalgae were harvested at their exponential growing phase and the cells suspension was centrifuged for the elimination of excess water and salts with a centrifuge of the type Alfa Laval CLARA 80. For the non-marine species the salt content was adjusted to achieve the same salt concentration as sea water. The cell slurries so obtained were subjected to drum drying to produce a microalgae biomass having a moisture content of approximately 50%.

For each microalgae species hundred grams of the drum dried biomass was extracted with 200 g of pure ethanol (99.9%) by stirring the blend of biomass and ethanol for 1 hour at room temperature using an Erlenmeyer flask with a magnetic stirrer and glass stopper. The extracts so obtained were filtered by suction with the help of a Büchner funnel and the retentates were washed twice with in total 50 g of ethanol. Next, more than 99 wt. % of the ethanol was removed from the filtrates using a rotational evaporator (65° C., 200 mbar).

After evaporation, the extracts were allowed to cool down to ambient temperature. At this stage phase separation occurred in all samples, yielding a biphasic extract comprising: an aqueous lower phase containing mainly salts and glycidic components; and an oily upper phase with a melting point of approximately 30° C.

The oil phases were separated from the aqueous phases by means of decanting. Analyses of these oil phases produced the following data:

| Microalgae | Lipids [#] | Eicosapentaenoic (EPA) or docosahexaenoic (DHA) | Carotenoids |
|---|---|---|---|
| *Isochrysis galbana* | 48.5 wt. % | 1 wt. % (DHA) | 1.88 wt. % |
| *Nannochloropsis gaditana* | 82.3 wt. % | 5.6 wt. % (EPA) | 4.1 wt. % |
| *Chlorella fusca* | 97.5 wt. % | 1.5 wt. % (EPA) | 1.3 wt. % |
| *Haematococcus pluvialis* | 96.6 wt. % | 1.4 wt. % (EPA) | 5 wt. % |

[#] Lipids = triglycerides, diglycerides, monoglycerides, phosphatides, free fatty acids

The invention claimed is:

1. A biphasic microalgal extract comprising 15-95 wt. % of an aqueous phase and 5-85 wt. % of an oil phase, said extract comprising at least 1% by total fatty acid weight of an ω3-fatty acid selected from the group consisting of eicosapentaenoic acid (EPA), docosahexaenoic acid (DHA) and a combination thereof, said extract further being characterized in that it comprises:
   (a) 40-100% lipids by weight of the oil phase, the lipids selected from the group consisting of triglycerides, diglycerides, monoglycerides, phosphatides, free fatty acids and combinations thereof;
   (b) 0.01-10% carotenoids by weight of the oil phase;
   (c) 0.5-10% sodium chloride by weight of the aqueous phase;
   (d) 0-3 wt. % non-dissolved material other than dispersed droplets of aqueous phase or oil phase; and
   (e) 0-10% $C_{1-5}$ monoalcohol by weight of the aqueous phase.

2. The extract according to claim 1, wherein at least 10 wt. % of the ω3 fatty acids are in a polar lipid selected from the group consisting of a phosphatide, a glycolipid and a combination thereof.

3. The extract according to claim 1, that comprises 0.01-10% $C_{1-5}$ monoalcohol by weight of the aqueous phase.

4. The extract according to claim 1, which is an extract of a microalgal species belonging to a microalgal genus or class selected from the group consisting of *Chysophyceae, Xantophyceae, Eustigmatophyceae, Baccilariophyceae, Dinophyceae, Rodophyceae, Phaeophyceae, Chlorophyceae, Prasinophyceae, Cryptophyceae, Botrycoccus, Isochrysis, Tetraselmis, Neochloris, Scenedesmus, Chlorobotrys, Eustigmatos, Pseudostaurastrum, Vischeria, Monodopsis, Ellipsoidion, Pseudocharaciopsis* and a combination thereof.

5. The extract according to claim 1, wherein 200 grams of the extract is fully soluble in 1 liter of $C_{1-5}$ monoalcohol.

6. The extract according to claim 1, that comprises at least 1%, by weight of dry matter, hydrolyzed cellulosic algal cell wall material.

7. A process of extracting an oil phase from a wet biomass of microorganisms, comprising:
   (a) combining the wet biomass with a solvent comprising at least 60 wt. % $C_{1-5}$ monoalcohol, said biomass comprising 10-95 wt. % water and 5-85%, by weight of dry matter, lipids selected from the group consisting of triglycerides, diglycerides, monoglycerides, phosphatides, free fatty acids and a combination thereof;
   (b) isolating a liquid phase from the combination of biomass and solvent, which liquid phase comprises:
      (i) 5-85 wt. % $C_{1-5}$ monoalcohol,
      (ii) 10-85 wt. % water and
      (iii) at least 5 wt. % dissolved and/or dispersed components originating from the biomass, including at least 5% lipids by weight of $C_{1-5}$ monoalcohol;
   (c) reducing the concentration of $C_{1-5}$ monoalcohol in the liquid phase to less than 10 wt. % while maintaining a water content of at least 15 wt. % to produce a biphasic extract comprising an aqueous phase and an oil phase; and
   (d) separating the oil phase from the aqueous phase.

8. The process according to claim 7, further comprising the step of reducing the concentration of the $C_{1-5}$ monoalcohol in the liquid phase by evaporation.

9. The process according to claim 7, wherein the biomass comprises at least 1%, by weight of total fatty acids, of a ω3-fatty acid selected from the group consisting of EPA, DHA and a combination thereof.

10. The process according to claim 7, wherein the wet biomass is a biomass of microalgae.

11. The process according to claim 1, wherein the microalgae belong to a genus or class selected from the group consisting of *Chysophyceae, Xantophyceae, Eustigmatophyceae, Baccilariophyceae, Dinophyceae, Rodophyceae, Phaeophyceae, Chlorophyceae, Prasinophyceae, Cryptophyceae, Botrycoccus, Isochrysis, Tetraselmis, Neochloris, Scenedesmus, Chlorobotrys, Eustigmatos, Pseudostaurastrum, Vischeria, Monodopsis, Ellipsoidion, Pseudocharaciopsis* and a combination thereof.

12. The process according to claim 7, wherein the biphasic extract produced in the process is a biphasic extract that comprises 15-95 wt. % of an aqueous phase and 5-85 wt. % of an oil phase, said extract containing at least 1% by total fatty acid weight of an ω3-fatty acid selected from the group consisting of EPA, DHA, and a combination thereof, said biphasic extract further being characterized in that it comprises:
- (a) 40-100%, by weight of the oil phase, lipids selected from the group consisting of triglycerides, diglycerides, monoglycerides, phosphatides, free fatty acids and a combination thereof;
- (b) 0.01-10% carotenoids by weight of the oil phase;
- (c) 0.5-10% sodium chloride by weight of the aqueous phase;
- (d) 0-3 wt. % non-dissolved material other than dispersed droplets of aqueous phase or oil phase; and
- (e) 0-10% $C_{1-5}$ monoalcohol by weight of the aqueous phase.

13. The process according to claim 7, wherein the oil phase is separated from the aqueous phase by centrifugation or decanting.

14. A process of extracting an oil phase from cell-wall-comprising microalgae, said oil phase comprising at least 1%, by weight of total fatty acids, of ω3-fatty acids selected from the group consisting of EPA, DHA and a combination thereof, the process comprising:
- (a) combining a wet microalgal biomass comprising the ω3-fatty acids with an enzyme preparation having cellulase, β-glucanase or β-glucosidase activity;
- (b) allowing the enzyme preparation to degrade the cell walls;
- (c) isolating from the enzyme-treated biomass at least 20% by weight of a liquid of the wet microalgae biomass, said liquid being a biphasic extract comprising 50-95 wt. % of an aqueous phase and 5-50 wt. % of an oil phase, said extract containing at least 1% by weight of total fatty acids of ω3-fatty acids selected from the group consisting of EPA, DHA and combinations thereof, said extract further being characterized in that it contains:
  - (i) 40-100% by weight of the oil phase of lipids selected from triglycerides, diglycerides, monoglycerides, phosphatides, free fatty acids and combinations thereof;
  - (ii) 0.01-10% of carotenoids by weight of the oil phase;
  - (iii) 0.5-10% of sodium chloride by weight of the aqueous phase;
  - (iv) 0-3 wt. % of non-dissolved material other than dispersed droplets of aqueous phase or oil phase; and
  - (v) 0-10% of $C_{1-5}$ monoalcohol by weight of the aqueous phase; and
- (d) separating the oil phase from the aqueous phase.

15. The process according to claim 14, wherein the enzyme preparation is combined with the biomass in an amount sufficient to provide at least 1 IU endoglucanase activity per gram of dry matter and/or at least 0.2 IU β-glucanase activity per gram of dry matter and/or at least 0.8 IU β-glucosidase activity per gram of dry matter.

16. The process according to claim 14, further comprising the step of reducing the concentration of the $C_{1-5}$ monoalcohol in the liquid phase by evaporation.

17. The process according to claim 14, wherein the biomass comprises at least 1%, by weight of total fatty acids, of ω3-fatty acids selected from the group consisting of EPA, DHA and a combination thereof.

18. The process according to claim 14, wherein the microalgae belong to a genus or class selected from the group consisting of *Chysophyceae, Xantophyceae, Eustigmatophyceae, Baccilariophyceae, Dinophyceae, Rodophyceae, Phaeophyceae, Chlorophyceae, Prasinophyceae, Cryptophyceae, Botrycoccus, Isochrysis, Tetraselmis, Neochloris, Scenedesmus, Chlorobotrys, Eustigmatos, Pseudostaurastrum, Vischeria, Monodopsis, Ellipsoidion, Pseudocharaciopsis* and a combination thereof.

19. The process according to claim 14, wherein the oil phase is separated from the aqueous phase by centrifugation or decanting.

* * * * *